US012708635B2

(12) United States Patent
Roscow

(10) Patent No.: US 12,708,635 B2
(45) Date of Patent: Aug. 18, 2026

(54) FORMULATIONS OF PSILOCYBIN AND PSILOCIN COMPOUNDS AS SEROTONIN AGONISTS IN COMBINATION WITH 3,4 METHYLENEDIOXYMETHAMPHETAMINE (MDMA)

(71) Applicant: Altrartis Therapeutics Inc., New York, NY (US)

(72) Inventor: Robert Fletcher Roscow, Longmont, CO (US)

(73) Assignee: ALTRARTIS THERAPEUTICS INC., New York, NY (US)

( * ) Notice: Subject to any disclaimer, the term of this patent is extended or adjusted under 35 U.S.C. 154(b) by 544 days.

(21) Appl. No.: 18/026,780

(22) PCT Filed: Sep. 18, 2021

(86) PCT No.: PCT/US2021/051005

§ 371 (c)(1),
(2) Date: Mar. 16, 2023

(87) PCT Pub. No.: WO2022/061196

PCT Pub. Date: Mar. 24, 2022

(65) Prior Publication Data

US 2023/0346811 A1 Nov. 2, 2023

Related U.S. Application Data

(60) Provisional application No. 63/080,679, filed on Sep. 18, 2020.

(51) Int. Cl.
*A61K 31/675* (2006.01)
*A61K 31/36* (2006.01)
*A61K 31/4045* (2006.01)

(52) U.S. Cl.
CPC ............ *A61K 31/675* (2013.01); *A61K 31/36* (2013.01); *A61K 31/4045* (2013.01)

(58) Field of Classification Search
CPC .................................................... A61K 31/675
See application file for complete search history.

(56) References Cited

U.S. PATENT DOCUMENTS

| | | | | |
|---|---|---|---|---|
| 6,106,864 | A | 8/2000 | Dolan | |
| 2015/0231126 | A1 | 8/2015 | Peters | |
| 2020/0147038 | A1* | 5/2020 | Russ | A61K 31/65 |
| 2023/0210762 | A1* | 7/2023 | Ameri | A61K 31/48<br>604/506 |

FOREIGN PATENT DOCUMENTS

| | | | |
|---|---|---|---|
| WO | 2000035298 | A1 | 6/2000 |
| WO | 2003000252 | A1 | 1/2003 |
| WO | WO2021074448 | * | 4/2021 |

OTHER PUBLICATIONS

Bleich. "The Role of Serotonin in Schizophrenia", Schizophrenia Bulletin, 1988, vol. 14(2), p. 297-315.

Brown. "Pharmacokinetics of Escalating Doses of Oral Psilocybin in Healthy Adults", Clin Pharmacokinet, 2017, V45, p. 1543-1554.

Gyllvik. "The Therapeutic Potential of Psilocybin and 3,4 Methylenedioxymethamphetamine in the Treatment of Depression and Post-Traumatic Stress Disorder" 1, 2, 4, 8, 9, 14-16, 19-25. University of Skovde. Jun. 2020, p. 1-37.

International Search Report and Written Opinion for PCT/US21/51005 mailed Feb. 16, 2022.

Mithoefer et al., MOMA-assisted psychotherapy for treatment of PTSD: study design and rationale for phase 3 trials based on pooled analysis of six phase 2 randomized controlled trials, Psychopharmacology, 2019, V236, p. 2735-2745.

Verma et al, Drug Delivery Technologies and Future Directions, Pharmaceutical Technology On-line, 2001, 25(2), p. 1-14.

Vollenweider, Brain mechanisms of hallucinogens and entactogens, vol. 3, Issue 4, pp. 265-279, 2001, Dialogues in Clinical Neuroscience.†

Licht, Simultaneous polysubstance use among Danish 3,4-methylenedioxymethamphetamine and hallucinogen users: combination patterns and proposed biological bases, vol. 27, issue 4, pp. 352-363, 2012, Human Psychopharmacology.†

Hokula, Jewel Mushrooms—Panaeolus cyaescens &MDMA, Apr. 9, 2002, Erowid Experience Vaults, Erowid Experience Vaults, URL: https://www.erowid.org/experiences/exp.php?ID=13584.†

Erowid, Psilocybin, Psilocin, and Magic Mushroom Dosage by Erowid, Sep. 15, 2016, Erowid, URL: https://erowid.org/plants/mushrooms/mushrooms_dose.shtml.†

Erowid, MDMA Dosage by Erowid, May 24, 2020, Erowid, URL: https://www.erowid.org/chemicals/mdma/mdma_dose.shtml.†

Blair, Effect of Ring Fluorination on the Pharmacology of Hallucinogenic Tryptamines, vol. 43, Issue 24, pp. 4701-4710, 2000, Journal of Medicinal Chemistry.†

* cited by examiner
† cited by third party

*Primary Examiner* — Rei Tsang Shiao
(74) *Attorney, Agent, or Firm* — Greenberg Traurig, LLP

(57) ABSTRACT

The present invention is directed to the use of psilocybin and/or psilocin compounds in combination with 3,4-methylenedioxymethamphetamine (MDMA) or other entactogens, to modulate activity of serotonin receptors, and preferably the 5-HT2A serotonin receptor in humans. In certain preferred embodiment, the co-formulation of psilocybin and/or psilocin compounds in combination with MDMA may result in complex modulation activity of serotonin receptors in a subject in need thereof, and may be uses as a therapeutic treatment for one or more serotonin receptor related diseases or conditions.

9 Claims, 4 Drawing Sheets

| | Psilocin only | MDMA only | Psilocin+MDMA 1:1 | Psilocin:MDMA 2:1 | Psilocin:MDMA 1:2 | Psilocin:MDMA 1:4 | Psilocin:MDMA 4:1 | Psilocin:MDMA 1:8 | Psilocin:MDMA 8:1 |
|---|---|---|---|---|---|---|---|---|---|
| EC50 | 0.000246 | 0.00003611 | 0.0001655 | 0.00003682 | 0.00004214 | 0.003447 | 0.0002321 | 0.0002344 | 0.00004268 |
| logEC50 | -3.609 | -4.442 | -3.781 | -4.434 | -4.375 | -2.463 | -3.634 | -3.63 | -4.37 |

| | EC50 | logEC50 |
| --- | --- | --- |
| Psilocin Only | 0.000246 | -3.609 |
| MDMA Only | 0.00003611 | -4.442 |
| Psilocin+MDMA-1:1 | 0.0001655 | -3.781 |
| Psilocin:MDMA-2:1 | 0.00003682 | -4.434 |
| Psilocin:MDMA-1:2 | 0.00004214 | -4.375 |

| | EC50 | logEC50 |
|---|---|---|
| Psilocin Only | 0.000246 | -3.609 |
| MDMA Only | 0.00003611 | -4.442 |
| Psilocin:MDMA-1:4 | 0.003447 | -2.463 |
| Psilocin:MDMA-4:1 | 0.0002321 | -3.634 |
| Psilocin:MDMA-1:8 | 0.0002344 | -3.63 |
| Psilocin:MDMA-8:1 | 0.00004268 | -4.37 |

FORMULATIONS OF PSILOCYBIN AND PSILOCIN COMPOUNDS AS SEROTONIN AGONISTS IN COMBINATION WITH 3,4 METHYLENEDIOXYMETHAMPHETAMINE (MDMA)

CROSS-REFERENCE TO RELATED APPLICATION

This application is a national stage application under 35 U.S.C. 371 of PCT Application No. PCT/US21/51005 having an international filing date of Sep. 18, 2021, which designated the United States, which PCT application claimed the benefit of U.S. Application Ser. No. 63/080,679, filed Sep. 19, 2020, both of which are incorporated by reference in their entirety.

TECHNICAL FIELD

The present invention is directed to psilocybin and psilocin tryptamine compounds, pharmaceutical compositions comprising such compounds, and methods of making and using the same. The invention is further directed to the use of tryptamine compounds in combination with 3,4-Methylenedioxymethamphetamine (MDMA) and/or other entactogens. The invention additionally presents the co-formulation of psilocybin, or psilocin and MDMA in order to provide the long-term relief seen with psilocybin treatment in tandem with the anxiety and fear reduction properties of MDMA.

BACKGROUND OF THE INVENTION

The serotonin 2A receptor (5-HT2A) has been implicated in mental disorders with complex etiologies that are still not clearly understood, in processes such as learning and memory and also in neurogenesis. The tryptamine compounds psilocybin and psilocin are known agonists of the 5-HT2A serotonin receptor. Activation of this receptor has been shown to provide benefit in therapies that address mental health disorders. However, potential negative side effects of psilocybin and psilocin include the possibilities of extreme anxiety, fear, sadness, and other negative emotions while under the influence of the substance.

MDMA is a known serotonin, norepinephrine and dopamine releasing agent, primarily acting by increasing the activity of neurotransmitters in parts of the brain. MDMA is considered an indirect non-selective serotonin receptor agonist that increases extracellular serotonin levels. MDMA is also known as an entactogen that directly interacts with the 5-HT2A serotonin receptor and has been shown to improve the treatment of mental health disorders in a therapy setting. Prior research in this area, while limited, suggests that 5-HT2A activation reduces pathogenic neural connectivity in patients and can result in symptom relief for months, or longer.

Given the extensive localization of this receptor to brain areas that mediate cognitive functions and social interaction, studies suggest that the 5-HT2A receptor might be involved in diseases in which these functions are impaired (generally referred to as serotonin receptor related disease(s) or condition(s)). Disorders in which the 5-HT2A receptor and/or serotonin levels seems to be involved range from schizophrenia, addictions, depression, obsessive compulsive disorder (OCD), cluster headaches, dementia, Alzheimer's disease, and paralysis and attention deficit-hyperactivity disorder (ADHD), to eating disorders such as anorexia nervosa, to autism spectrum disorders among others.

Evidence to support such connections varies from genetic screens to binding and protein expression data and some molecular data. Further, additional studies conducted with MDMA, researchers recently concluded the drug was successful in treating PTSD in a majority of participants. Additionally, MDMA has been noted for its anxiolytic (anti-anxiety) properties. Previous clinical trials have also looked at the positive effects MDMA can have on individuals with depression and anxiety due to life-threatening illnesses. However, as noted above, administration of tryptamines such as psilocybin or psilocin may include severe side-effects limiting the compounds therapeutic uses.

However, administration of a second serotonin agonist, such as the indirect serotonin agonist MDMA, may generate an additive effect increasing the potential for over-activation of serotonin receptors leading to unwanted negative side effects. MDMA or other entactogens also exhibit dual action as Monoamine Oxidase Inhibitors (MAOIs). MAOIs are a class of drugs that inhibit the activity of one or both monoamine oxidase enzymes: monoamine oxidase A (MAO-A) and monoamine oxidase B (MAO-B). They are best known as anti-depressants, as well as effective therapeutic agents for panic disorder and social phobia.

As can be seen, there is a long-felt need for an improved therapeutic treatment for serotonin receptor related diseases or conditions that can allows for the benefits of tryptamine compounds, such as psilocin, while ameliorating its negative side-effects. The invention posits combining MDMA or other entactogens with tryptamines such as psilocybin or psilocin may promote complex modulation of serotonin receptors. For example, MDMA may reduce the negative side-effects of, for example psilocybin or psilocin. In certain embodiments, the invention includes the co-formulation of psilocybin and MDMA, thus providing the long-term relief seen with psilocybin treatment combined with the anxiety and fear reduction properties of MDMA. It is anticipated that the combination of these effects may render a significantly improved drug for use as an adjunct to therapy.

SUMMARY OF THE INVENTION

The invention include novel methods and compositions for combining MDMA or other entactogens with tryptamines such as psilocybin or psilocin that may promote complex activation of serotonin receptors, such as 5-HT2A. For example, combining MDMA or other entactogens with tryptamines such as psilocybin or psilocin may demonstrate complex serotonin receptor activation resulting in the activation of a of serotonin receptor that is approximately the same as the level of receptor activation that would be seen from only the psilocybin or psilocin compounds. It should be noted that in some aspects, psilocybin may be administered to a subject or cell of a subject, wherein the compound is metabolized to psilocin. In such instances, the terms psilocybin and psilocin are considered equivalent.

In one preferred aspect, the invention include novel methods and compositions for combining MDMA or other entactogens with tryptamines such as psilocybin or psilocin that may promote complex activation of serotonin receptors, such as 5-HT2A, further resulting in a novel therapeutic presentation. For example, combining MDMA or other entactogens with tryptamines such as psilocybin or psilocin may demonstrate complex serotonin receptor activation resulting in a therapeutic response that result in the reduction or elimination of one or more of the negative side effects of the psilocybin or psilocin compounds in a subject in need thereof. In another aspect, a ratio of psilocybin to MDMA, with the intention to limit negative emotional outcome. In another aspect, any ratio of any tryptamine to MDMA, with the intention to limit negative emotional outcome. In another aspect, MDMA and psilocybin delivered individually during the course of treatment to limit negative emotions during treatment or after. In another aspect, MDMA used in an alternating schedule with psilocybin for promotion of therapy effectiveness and longevity.

Additional aspect of the invention will become apparent through the following preferred embodiments described in the claims, figures and specification below.

BRIEF DESCRIPTION OF THE FIGURES

FIGS. 4A-B: (A) Initial metabolic pathway conversion of psilocybin result in conversion of psilocin (B) Chemical formula for MDMA, including racemic, R and S forms.

DETAILED DESCRIPTION OF THE INVENTION

Figures 1A, 1B:
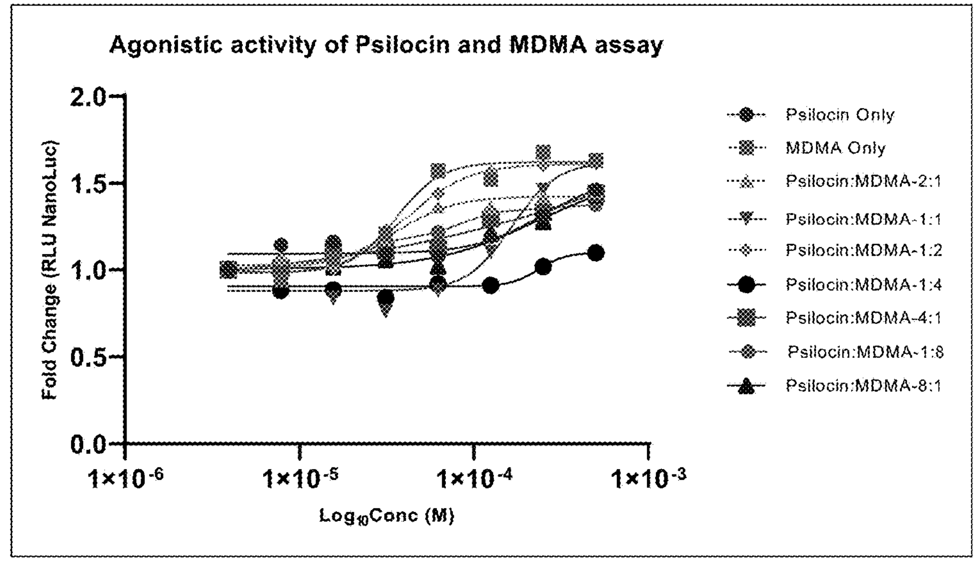
FIGS. 1A-B: (A) graphical demonstration of 5-HT2A receptor agonistic activity of psilocin, MDMA and different ratios of psilocin/MDMA mixtures; (B) summary of EC50 and logEC50 values for agonistic activity of psilocin, MDMA and different ratios of Psilocin/MDMA mixtures.

The invention may include novel methods and compositions for modulating serotonin receptor activity in a cell, and preferably a human cell. In one preferred aspect, the invention may include a pharmaceutical compositions containing a therapeutically effective amount of a tryptamine compound and an entactogen compound, and at least one pharmaceutically acceptable carrier, wherein the entactogen compound alleviates one or more negative side-effects of the tryptamine. In this embodiment, the novel methods and compositions for modulating serotonin receptor activity may be used to treat a human subject suffering from, or at risk from suffering from serotonin receptor related disease or condition.

Another embodiment of the invention may include novel methods and compositions for modulating serotonin receptor activity in a cell, and preferably a human cell. In one preferred embodiment, the invention may include a pharmaceutical compositions containing a therapeutically effective amount of a tryptamine compound and an entactogen compound, and at least one pharmaceutically acceptable carrier, wherein the formulation of the tryptamine compound and an entactogen compound activates a serotonin receptor, and preferably the serotonin receptor 5-HT2A, in a subject to approximately the same level as the activation by the tryptamine compound alone, without in the absence of the entactogen. In this embodiment, the novel methods and compositions for modulating serotonin receptor activity may be used to treat a human subject suffering from, or at risk from suffering from serotonin receptor related disease or condition.

Another embodiment of the invention may include novel methods and compositions for modulating serotonin receptor activity in a cell, and preferably a human cell. In one preferred embodiment, the invention may include a pharmaceutical compositions containing a therapeutically effective amount of a psilocybin, or psilocin compound and an MDMA, and at least one pharmaceutically acceptable carrier, wherein the MDMA compound alleviates one or more negative side-effects of psilocybin, or psilocin. In this embodiment, the novel methods and compositions for modulating serotonin receptor activity may be used to treat a human subject suffering from, or at risk from suffering from serotonin receptor related disease or condition.

Another embodiment of the invention may include novel methods and compositions for modulating serotonin receptor activity in a cell, and preferably a human cell. In one preferred embodiment, the invention may include a pharmaceutical compositions containing a therapeutically effective amount of a psilocybin, or psilocin compound and an MDMA compound, and at least one pharmaceutically acceptable carrier, wherein the formulation of the psilocybin, or psilocin compound and an MDMA compound activates a serotonin receptor, and preferably the serotonin receptor 5-HT2A, in a subject to approximately the same level as the activation by the psilocybin, or psilocin compound alone, without in the absence of the MDMA. In this embodiment, the novel methods and compositions for modulating serotonin receptor activity may be used to treat a human subject suffering from, or at risk from suffering from serotonin receptor related disease or condition.

Another embodiment of the invention may include novel formulations for modulating serotonin receptor activity in a cell, and preferably a human cell. In one preferred embodiment, the invention may include a compositions, and preferably a pharmaceutical compositions having a therapeutically effective amount of a tryptamine compound and an entactogen compound, wherein the tryptamine compound and an entactogen compound modulate activity of a 5-HT2A serotonin receptor in a subject, and wherein said serotonin receptor is activated to approximately the same level as the activation by said tryptamine compound without said entactogen. In one embodiment, the composition may include a ratio of a tryptamine compound and entactogen compound is approximately equal, while in alternative embodiments the composition may include a ratio of a tryptamine compound and entactogen compound where the amount of tryptamine or entactogen is higher compared to the other. In this preferred embodiment, the composition may include a ratio of a tryptamine compound and entactogen compound that selected from the group consisting of: 1:1; 4:1; 1:8, 1:1-1:8; 1:1 to 4:1, 1:1 to 6:1, and 1:1 to 1:10. In this embodiment, the novel formulations for modulating serotonin receptor activity may be used to treat a human subject suffering from, or at risk from suffering from serotonin receptor related disease or condition.

Another embodiment of the invention may include novel formulations for modulating serotonin receptor activity in a cell, and preferably a human cell. In one preferred embodiment, the invention may include a compositions, and preferably a pharmaceutical compositions having a therapeutically effective amount of a psilocybin or psilocin compound and an MDMA compound, wherein said psilocybin, or psilocin compound and an MDMA compound modulate activity of a 5-HT2A serotonin receptor in a subject, and wherein said serotonin receptor is activated to approximately the same level as the activation by said psilocybin, or psilocin compound without said MDMA. In one embodiment, the composition may include a ratio of psilocybin or psilocin and MDMA is approximately equal, while in alternative embodiments the composition may include a ratio of psilocybin or psilocin and MDMA where the amount of psilocybin/psilocin or MDMA is higher compared to the other. In this preferred embodiment, the composition may include a ratio of psilocybin or psilocin compound and MDMA compound that selected from the group consisting of: 1:1; 4:1; 1:8, 1:1-1:8; 1:1 to 4:1, 1:1 to 6:1, and 1:1 to 1:10. In this embodiment, the novel formulations for modulating serotonin receptor activity may be used to treat a human subject suffering from, or at risk from suffering from serotonin receptor related disease or condition.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

As used herein, a "serotonin receptor agonists" means a substance, and preferably a compound of the invention, having the function of acting directly or directly on a serotonin receptor, such as preferably the 5-HT2A receptor, causing an increase in amount of serotonin released into the synapses of a subject. As used herein, an "agonist" means a substance, and preferably a compound of the invention, having the function of binding/activating to a receptor or to produce a biological response. The "serotonin receptor agonists" or "agonist" of the invention used in the methods of treatment according to the invention can be: (1) an tryptamine or entactogen as described herein, or a pharmaceutically acceptable salt thereof, a prodrug thereof, or a metabolite thereof, (2) a compound which was known prior to the present invention, but wherein it was not known that the compound is an agonist of the 5-HT2A serotonin receptor, an entactogen, or a pharmaceutically acceptable salt thereof, a prodrug thereof, or a metabolite thereof; or (3) a compound which was known prior to the present invention, and wherein it was known that the compound is an agonist of the 5-HT2A serotonin receptor, or an entactogen, but wherein it was not known that the compound is useful for the methods of treatment described herein, or a pharmaceutically acceptable salt thereof, a prodrug thereof, or a metabolite thereof.

In some embodiments, the pharmacological mechanism of 5-HT2A activity and the release of native serotonin, dopamine and norepinephrine, are accomplished with a single active pharmaceutical ingredient. It is the novel compilation of these mechanisms, for reasons stated above, that is useful in therapy for improved outcomes. Compounds administered include but are not limited to: a-methyltryptamine, 5-methoxy-a-methyltryptamine, a-ethyltryptamine, 5-methoxy-a-ethyltryptamine, 6-fluoro-a-methyltryptamine, 4,a-dimethyl tryptamine, 4-hydroxy-a-methyltryptamine, 4-methyl-a-ethyltryptamine, 7-methyl-a-ethyltryptamine, 5-chloro-a-methyltryptamine and a,N,N-trimethyltryptamine.

In yet another embodiment, use of an entactogen (serotonin or dopamine releasing agent) with cross reactivity at 5-HT2A for therapy: examples include, but are not limited to alphaMT, 5-MeO-alphaMT, alphaET, 5-MeO-alphaET, 6-Fluoro-alphaMT, 4-Methyl-alphaMT, 4-Hydroxy-alphaMT, 4-Methyl-alphaET, 7-Methyl-alphaET, 5-cloro-alphaMT, alphaTMT.

As used herein, a "serotonin receptor related disease or condition" includes a disease or condition in a subject, and preferably a human subject for which administration of a serotonin receptor is beneficial, or for which modulation of the serotonin receptor's activity results in improved outcomes in the subject.

The subject can be any animal, domestic, livestock or wild, including, but not limited to cats, dogs, horses, pigs and cattle, and preferably human subjects, and even more preferably a human subject suffering from, or at risk of suffering from one or more serotonin receptor related diseases or conditions. As used herein, the terms patient and subject may be used interchangeably.

The term "modulation" or "modulate" as used herein in the context of a serotonin, or other receptor binding, refers to a change in activation state as compared to the absence of a compound of the invention, or a patent compound of one or more of the compounds of the invention. In one embodiment, modulation of a serotonin, such as 5-HT2A may by effectuated by an agonist compounds and result in its activation.

The "therapeutically effective amount" for the treatment of a subject afflicted with a disorder ameliorated by the described therapy is an amount that causes amelioration of the disorder being treated or protects against a risk associated with the disorder, and in particular a serotonin receptor related disease or condition. For example, for schizophrenia, a therapeutically effective amount is an amount which causes a significant reduction in psychopathology as determined by clinical improvement; for depression, a therapeutically effective amount is an amount that leads to stabilization and remission of symptoms as measured by the Patient Health Questonnaire-9; for OCD, a therapeutically effective amount is an amount that leads to stabilization and remission of symptoms as measured by the Yale-Brown Obsessive Compulsive Scale; for ADHD, a therapeutically effective amount is an amount that leads to stabilization and remission of symptoms as measured by either the ADHD Rating Scale V or ADHD Self-Report Scale; for eating disorders, a therapeutically effective amount is an amount that leads to stabilization and remission of symptoms as measured by the Eating Disorder Examination Questionnaire; for autism spectrum disorders a therapeutically effective amount is an amount that leads to stabilization and remission of symptoms as measured by physicians' assessment; for PTSD a therapeutically effective amount is an amount that leads to stabilization and remission of symptoms as measured by the Clinician-Administered PTSD Scale for DSM-5; for anxiety, a therapeutically effective amount is an amount that leads to stabilization and remission of symptoms as measured by the General Anxiety Disorder-7; for addiction, a therapeutically effective amount is an amount that leads to stabilization and remission of symptoms as measured by physicians' assessment; for cluster headaches, a therapeutically effective amount is an amount that leads to stabilization and remission of symptoms as measured by the Cluster Headache Severity Scale (CHSS); for dementia, a therapeutically effective amount is an amount that leads to stabilization and remission of symptoms as measured by the Dementia Rating Scale (DRS); for Alzheimer's disease, a therapeutically effective amount is an amount that leads to stabilization and remission of symptoms as measured by the Alzheimer's Disease Assessment Scale-Cognitive Subscale (ADAS-Cog); for paralysis, a therapeutically effective amount is an amount that leads to stabilization and remission of symptoms as measured by physicians' assessment.

As used herein, "treating" or "treatment" describes the management and care of a patient for the purpose of combating a disease, condition, or disorder, and in particular serotonin receptor related disease or condition and includes the administration of a compound or pharmaceutical compositions of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, or other abnormal condition, and in particular a serotonin receptor related disease or condition. Treatment is continued as long as symptoms and/or pathology ameliorate. The term "beneficial" or "improved outcomes" as used herein in the context of treating a condition, refers to extended relieve of symptoms (duration) and/or a more significant reduction of symptoms (magnitude), and in particular with respect to a serotonin receptor related disease or disorder. Exemplary serotonin receptor related diseases or disorders can include schizophrenia, depression, obsessive compulsive disorder, attention deficit-hyperactivity disorders, eating disorders, autism spectrum disorders, PTSD and anxiety as discussed above. The phrase "improved outcomes" means an extended relieve of symptoms (duration) and/or a more significant reduction of symptoms (magnitude).

The term "MDMA" is interchangeable with other entactogens such as 3,4 methylenedioxyamphetamine, 2,5-dimethoxy-4-bromophenethylamine, 3, 4-methylenedioxyN-ethylamphetamine, a-methyltryptamine and a-ethyltryptamine.

Figures 4A, 4B:
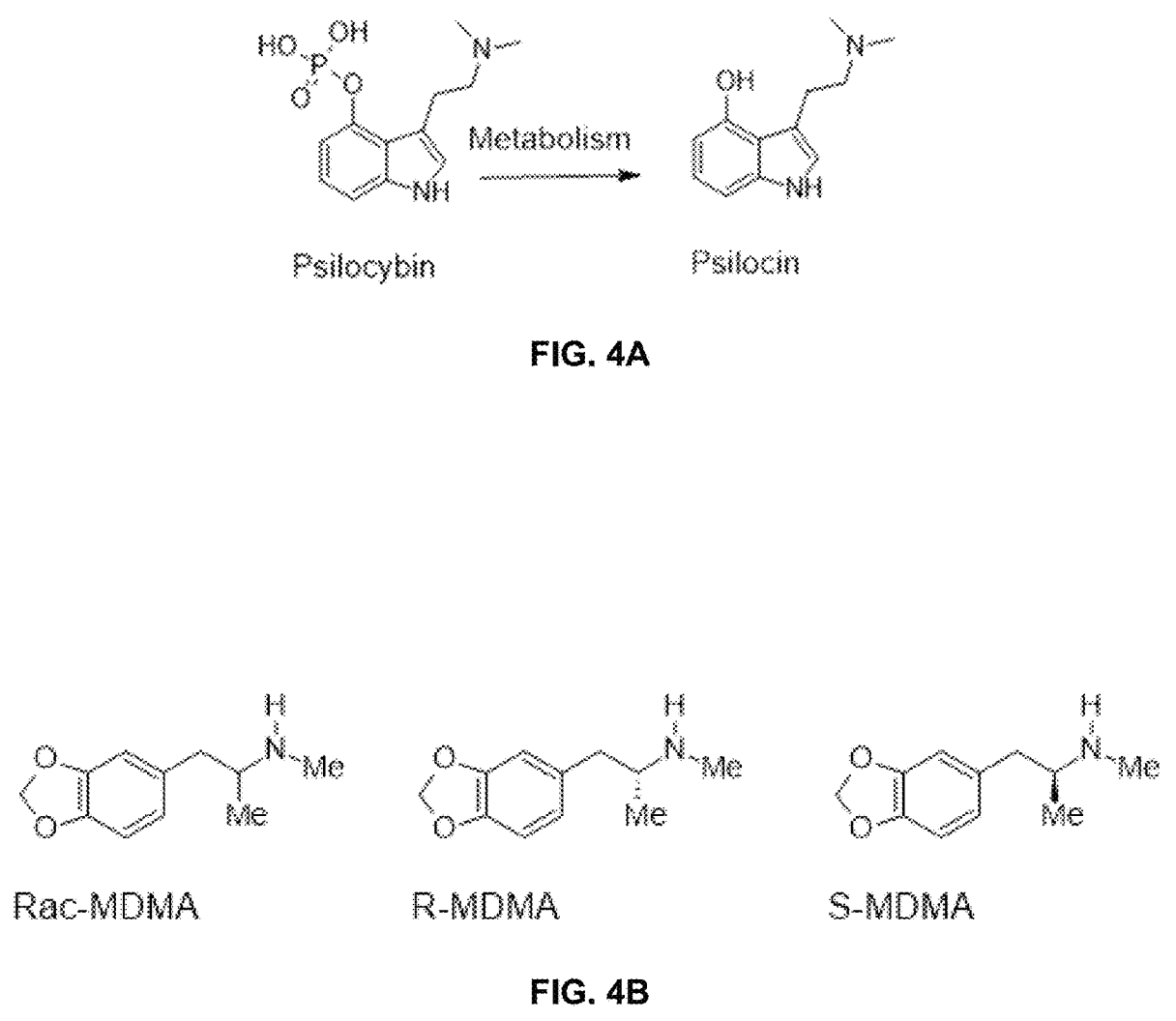

The terms "psilocybin" and "psilocin" are shown in FIG. 4, and are interchangeable with the tryptamines listed below.

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

As used herein, "tryptamine" means compounds having affinity for a serotonin receptor and may include, but not be limited to: substituted tryptamines, psilocybin, psilocin, N,N-dimethyltryptamine, 5-methoxy-N,N-dimethyltryptamine, N,N-Dipropyltryptamine, 5-methoxy-N,N-Dipropyltryptamine, baeocystin ([3-[2-(methylamino)ethy 1]-1 H-indol-4-yl] dihydrogen phosphate), norbaeocystin ([3-(2-aminoethyl)-1H-indol-4-yl] dihydrogen phosphate), aeruguinascin (N,N,N-trimethyl-4-phosphorl-oxytryptamine), 4-acetoxy-N,N-dimethyltryptamine, 3-(2'-dimethylaminoethy 1)-4-acetoxy-indole.

As used herein, "entactogens" means a compounds having the effect of releasing serotonin, norepinephrine and dopamine such as 3,4-methylenedioxyamphetamine (MDMA), 2,5-dimethoxy-4-bromophenethylamine, 3,4-methylenedioxyN-ethylamphetamine, a-Ifamethyltryptamine and alpha-ethyltryptamine. Included in the list of tryptamines are compounds with similar binding affinities to serotonin receptors.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary, shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

The present invention proposes the use of a combination of drug dosage in a two part pill or capsule where the time release properties of the two compounds are controlled. To compensate for the different timing of the compounds to reach full physiological effect, these properties can be held static or delivered with an enhanced bioavailability formulation. Additionally, the present invention proposes that the delivery of the entactogen component may be such that the anxiolytic effect may be present prior to and sustained until post intoxication with the psilocybin or tryptamine component.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrants will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents. Exemplary tablets contain up to about 80 wt % drug, from about 10 wt % to about 90 wt % binder, from about O wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated. The formulation of tablets is discussed in detail in “Pharmaceutical Dosage Forms: Tablets, Vol. 1”, by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release. Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low.

Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams, or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. In general, the dosage, i.e., the therapeutically effective amount, ranges from 1 μg to 10 g/kg and often ranges from 10 μg to 1 g/kg or 10 μg to 200 mg/kg body weight of the subject being treated, per day.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound, for example a composition of the invention, and preferably a serotonin receptor agonist, such as a tryptamine and/or entactogen, and more preferably psilocin and MDMA, calculated to produce the desired therapeutic effect in association with the required pharmaceutical carrier. The specification for the dosage unit forms of the invention are dictated by and directly dependent on (a) the unique characteristics of the composition and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a subject in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of serotonin receptor agonists, such as a tryptamine and/or entactogen, and more preferably psilocin and MDMA are well-known in the relevant art and would be understood to be encompassed by the skilled artisan once provided the teachings disclosed herein.

The amount of a composition of the invention, and preferably a serotonin receptor agonist, such as a tryptamine and/or entactogen, and more preferably psilocin and MDMA of the invention, administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0. 7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day. In one preferred embodiment, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Administration of a composition of the invention, and preferably a bivalent composition of the invention, may be effected by any method that enables delivery of the compositions to the site of action. These methods include oral routes, intraduodenal routes, parenteral injection (including intravenous, subcutaneous, intramuscular, intravascular or infusion), topical, and rectal administration.

In subjects with irregular serotonin production and/or extreme anxiety, fear or sadness, modulation of these symptoms may be achieved, for example, by administering one or more of the disclosed compounds that increase serotonin levels. In one embodiment, in subjects with irregular serotonin production and/or extreme anxiety, fear or sadness, modulation of these symptoms may be achieved, for example, by administering to a subject in need thereof, a tryptamines and an entactogens, and preferably psilocybin or psilocin and MDMA. In another embodiment, subjects with irregular serotonin production and/or extreme anxiety, fear or sadness, modulation of these symptoms may be achieved, for example, by administering one or more of the disclosed compounds that increase serotonin levels, such compounds may be administered with other tryptamines such as a-methyltryptamine, 5-methoxy-amethyltryptamine, a-ethyltryptamine, 5-methoxy-a-ethyltryptamine, 6-fluoro-amethyltryptamine, 4,a-dimethyltryptamine, 4-hydroxy-a-methyltryptamine, 4-methyl-aethyltryptamine, 7-methyl-a-ethyltryptamine, 5-chloro-a-methyltryptamine and a,N, Ntrimethyltryptamine and/or entactogens, such as methylenedioxyamphetamine (MDA), 2,5-dimethoxy-4-bromophenethylamine and 3,4-methylenedioxy-N-ethylamphetamine, as described in detail herein.

The invention now being generally described will be more readily understood by reference to the following examples, which are included merely for the purposes of illustration of certain embodiments of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine, and the like.

The terms "approximately" and "about" refer to a quantity, level, value, or amount that varies by as much as 30%, or in another embodiment by as much as 20%, and in a third embodiment by as much as 10% to a reference quantity, level, value, or amount. As used herein, the singular form "a," "an," and "the" include plural references unless the context clearly dictates otherwise. In the context of "approximate" receptor activation, this terms means that the receptor activity will generate approximately the same physiological result as compared to a different receptor activation condition.

As used herein the singular forms "a", "an", and "the" include plural referents unless the context clearly dictates otherwise. Thus, for example, reference to "a cell" includes one or more cells and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value. In addition, the term "between" includes all ranges within the stated number range provided. For example, throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The invention described herein suitably may be practiced in the absence of any element(s) not specifically disclosed herein. Thus, for example, in each instance herein any of the terms "comprising", "consisting essentially of", and "consisting of" may be replaced with either of the other two terms. All ratios provided herein as considered approximate.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Efficacy of Combined Psilocin/MDMA in Serotonin Receptor Activation The present inventors demonstrated the in vivo synergistic modulation of serotonin receptor 5HT2A activity in response to a tryptamine compound and an entactogen. Specifically, the present inventors seeded human HEK293 cells in DMEM media with 1% penicillin/streptomycin and 10% FBS in a 10 $cm^2$ plate at initial concentration of $3\times10^6$. Cells were transfected with expression vectors using Lipofectamine-2000. DNA concentrations were standardized to 3 μg of receptor DNA (5HT2A) and 6 μg of plasmids expressing other proteins for assay. Two days after the transfection cells were washed with D-PBS and resuspended in D-PBS with 5 mM-Glucose. In total, 45 μl/well was seeded into a 96-well plate to reach the final cell count of 30-40K cells/well and supplemented with 5 μM of Furimazine. After 5 minutes of incubation at room temperature, 5HT2A receptor ligand was added, and luminescence was measured every 2 minutes for kinetic data. Data was analyzed using GraphPad Prism. Transient transfection data was normalized to fold change of basal luminescence and ER50 and logEC50 were calculated.

As shown in FIGS. 1-3, baseline 5HT2A receptor activation for psilocin and MDMA was established. Multiple ratios psilocin and MDMA was further tested, having the same molarity to determine the 5HT2A receptor activation for each combination. As specifically shown in FIGS. 1-3, the combination administration of psilocin and MDMA did not shown an obvious additive effect in 5HT2A receptor activation demonstrating a complex mitigating interaction between the interaction of psilocin and MDMA on the serotonin receptor activation.

Figures 2A, 2B:
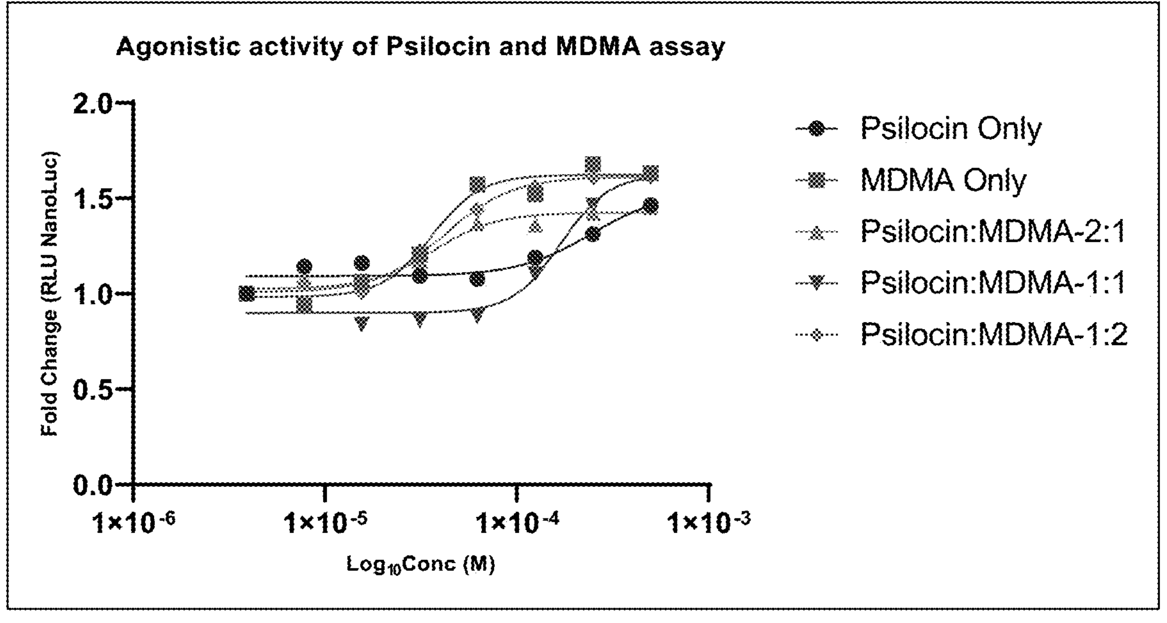
FIGS. 2A-B: (A) graphical demonstration of 5-HT2A receptor agonistic activity of psilocin, MDMA and different ratios of psilocin/MDMA mixtures; (B) summary of EC50 and logEC50 values for agonistic activity of psilocin, MDMA and different ratios of Psilocin/MDMA mixtures.

As specifically shown in FIG. 2B, the ratio psilocin:MDMA 1:1 generated nearly the same 5HT2A receptor activation as psilocin alone. These data shown that approximately the same 5HT2A receptor activation can be achieved through the combine use of psilocin and MDMA, wherein the amount of psilocin is present in a lower amount compared to psilocin-only activation.

Figures 3A, 3B:
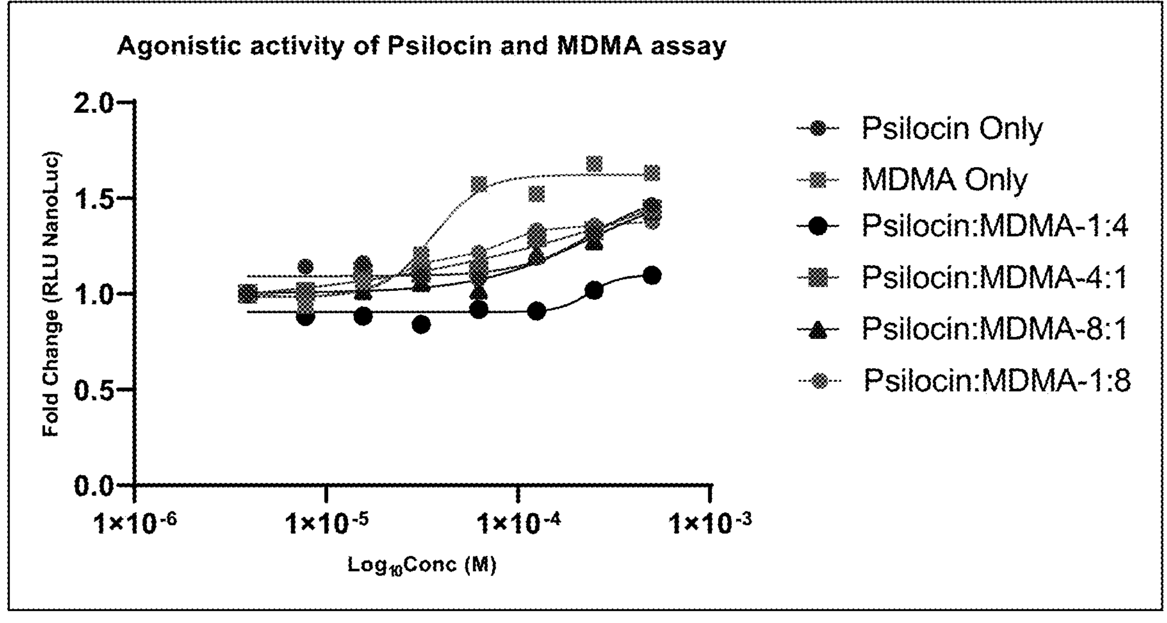
FIGS. 3A-B: (A) graphical demonstration of 5-HT2A receptor agonistic activity of psilocin, MDMA and different ratios of psilocin/MDMA mixtures; (B) summary of EC50 and logEC50 values for agonistic activity of psilocin, MDMA and different ratios of Psilocin/MDMA mixtures.

As specifically shown in FIG. 3B, the ratio psilocin:MDMA 4:1 generated nearly the same 5HT2A receptor activation as psilocin alone. These data shown that approximately the same 5HT2A receptor activation can be achieved through the combine use of psilocin and MDMA, wherein the amount of psilocin is present in a lower amount compared to psilocin-only activation.

As further shown in FIG. 3B, the ratio psilocin:MDMA 1:8 generated nearly the same 5HT2A receptor activation as psilocin alone. These data shown that approximately the same activation can be achieved through the combine use of psilocin and MDMA, wherein MDMA is present in a significantly higher amount compared to psilocin-only activation.

The above data demonstrate that a therapeutically effective amounts of different serotonin agonists, such as a tryptamine and an entactogen compound can be administered to a subject in need thereof, resulting in the serotonin receptor activation that is approximately the same as a activation generated by a serotonin agonists.

The above data demonstrate that a therapeutically effective amounts of tryptamine compound and an entactogen compounds, such as psilocin, or its pre-metabolized form psilocybin and MDMA can be administered to a subject in need thereof, resulting in the serotonin receptor activation that is approximately the same as psilocin-only activation.

In one embodiment, the efficacy and success rate of treatment in care of serotonin receptor related disease or condition between placebo, MDMA alone, psilocybin alone, and the compound/s of this invention, and preferably a combination of MDMA alone, psilocybin/psilocin. A very low dose of the compound can be used as an active control, or a general placebo can be used. A standard therapy for a specific illness will be chosen, for example Exposure and Response Prevention for Obsessive Compulsive Disorder or using Cognitive Behavioral Therapy. Patients will be followed longitudinally, with tracking of the severity of their condition overtime, as well as the success or failure rate in tolerating the treatment. Patients will also be directly assessed regarding anxiety before during and after the course of treatment. Additionally, the study therapists will be asked to qualitatively rate each treatment type, in regard to improvement over the standard treatment regime.

What is claimed is:

1. A composition for treating a serotonin receptor related disease or condition in a subject in need thereof, comprising a therapeutically effective amount of psilocybin or psilocin and 3,4-methylene-dioxymethamphetamine (MDMA), wherein the psilocybin or psilocin and the MDMA modulate activity of a 5-HT2A serotonin receptor in said subject, wherein said serotonin receptor is activated to approximately the same level as the activation by psilocybin or psilocin without MDMA, and wherein said composition additionally comprises at least one pharmaceutically acceptable carrier.

2. The composition of 1, wherein the MDMA alleviates one or more negative side-effects of the psilocybin or psilocin.

3. The composition of 1, wherein the ratio of psilocybin or psilocin and MDMA is selected from the group consisting of: 1:1; 4:1; 1:8, 1:1 to 1:8; 1:1 to 4:1, 1:1 to 6:1, and 1:1 to 1:10.

4. The composition of claim 1, wherein said serotonin receptor related disease or condition is selected from the group consisting of: schizophrenia, addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

5. The composition of claim 1, wherein the psilocybin or psilocin and the MDMA are administered under controlled time-release conditions.

6. The composition of claim 1, wherein the MDMA is provided in a time release condition such that it is present prior to intoxication with the psilocybin or psilocin.

7. The composition of claim 6, wherein the MDMA is sustained until post intoxication with the psilocybin or psilocin.

8. The composition of claim 1, wherein the dose of the psilocybin or psilocin is in a dosage range of 10 μg to 1 g/kg, or 10 μg to 200 mg/kg body weight of the subject being treated, per day.

9. The composition of claim 1, wherein the dose of the MDMA is in a dosage range of 10 μg to 1 g/kg, or 10 μg to 200 mg/kg body weight of the subject being treated, per day.

* * * * *